US006969616B2

(12) United States Patent
Hirai et al.

(10) Patent No.: US 6,969,616 B2
(45) Date of Patent: Nov. 29, 2005

(54) ENTEROTOXIN ADSORBENT, METHOD OF ADSORPTIVE REMOVAL, AND ADSORPTION APPARATUS

(75) Inventors: Fumiyasu Hirai, Ibaraki (JP); Tamiji Fujimoto, Settsu (JP); Shigeo Furuyoshi, Kobe (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/961,414

(22) Filed: Sep. 25, 2001

(65) Prior Publication Data

US 2002/0058032 A1 May 16, 2002

(30) Foreign Application Priority Data

Sep. 26, 2000 (JP) ....................................... 2000-291830

(51) Int. Cl.[7] ...................... G01N 33/538; A61K 39/02; A61K 39/085; A61K 39/00

(52) U.S. Cl. ................. 436/541; 424/236.1; 424/237.1; 424/140.1

(58) Field of Search ........................... 424/236.1, 237.1, 424/140.1; 436/541

(56) References Cited

U.S. PATENT DOCUMENTS 3,525,731 A 8/1970 Stojanow et al.

FOREIGN PATENT DOCUMENTS

| | | | |
|---|---|---|---|
| EP | 0 743 067 A2 | * | 11/1996 |
| EP | 0093 834 A | * | 4/2000 |
| EP | 0 933 834 A1 | * | 4/2000 |
| EP | 0 993 834 A1 | * | 4/2000 |
| WO | WO 97/27889 | * | 8/1997 |

OTHER PUBLICATIONS

Schlievert et al ,Journal of Infectious Diseases, May 1993, 167(5):997–1002.*

McLauchlin et al, Journal of Food Prot, Apr. 2000; 63(4):479–488.*

Mehrotra et al, Journal of Clinical Microbiology, Mar. 200, p. 1032–1035.*

Nagaki et al, Journal of Med. Microbiol, vol. 38, 1993, 354–359.*

Nagaki et al, Journal of Medical Microbiology, May 1993, 38(5): 354–359.*

* cited by examiner

*Primary Examiner*—Nita Minnifield
*Assistant Examiner*—Vanessa L. Ford

(57) ABSTRACT

The present invention is directed to an enterotoxin adsorbent comprising a compound having a log P (P denotes a partition coefficient in an octanol-water system) value of not less than 2.50 as immobilized on a water-insoluble carrier.

6 Claims, 2 Drawing Sheets

ENTEROTOXIN ADSORBENT, METHOD OF ADSORPTIVE REMOVAL, AND ADSORPTION APPARATUS

FIELD OF THE INVENTION

The present invention relates to an enterotoxin adsorbent, a method for adsorptive removal of an enterotoxin, and an adsorption apparatus comprising said adsorbent as packed in a housing.

BACKGROUND OF THE INVENTION

Enterotoxins are toxins produced by *Staphylococcus aureus*, among other bacteria, which have various biological activities such as emetic, pyrogenic and mitogenic activities, inducing symptoms of food poisoning or being causative of toxic shock syndrome (TSS).

Staphylococci are broadly distributed in the skin, nasal cavity, oral cavity, throat, urinary organs and intestinal canal of various animals inclusive of man as well as in the air, sewage water, river, foods and so forth and encompass a broad spectrum of species. Among such numerous species of staphylococci, the one pathogenic to human beings is *Staphylococcus aureus* (hereinafter referred to briefly as *S. aureus*) which is a coagulase-positive bacterium. *S. aureus* induces various infectious diseases and can be a causative factor in nosocomial infections, thus being of social concern.

As the enterotoxin produced by *S. aureus*, the following 10 species are known to this day: staphylococcal enterotoxins A, B, C1, C2, C3, D, E, G, H and I (hereinafter referredtobriefly as SEA, SEB, SEC1, SEC2, SEC3, SED, SEE, SEG, SEH and SEI, respectively).

Enterotoxins are known to have superantigen activity. The ordinary antigen is taken up by the antigen-presenting cell and the antigen fragments available on fragmentation (conversion to peptides of 10 to 15 amino acids) are presented, in the form bound to the pockets of MHC (major histocompatibility complex) class II molecule, on the surface of the antigen-presenting cell. These fragments are recognized by the TCR (T cell receptor) α- and β-chains of certain T cell clones, whereby the T cells are activated to set an immune reaction going. On the other hand, in the case of a superantigen, the antigen is not fragmented but directly-bound to the MHC class II molecule on an antigen-presenting cell, and then the complex is recognized by TCR on the T cell to thereby activate the T cell. In this process, the antigen is recognized by the Vβ region of the TCR but unlike in the case of an ordinary antigen, the superantigen is recognized by substantially the entire population of T cells expressing the specific Vβ region to induce activation of the T cells and, hence, production of cytokines. Thus, in an individual exposed to a superantigen, an enormous population of T cells is activated as compared with the ordinary specific immune response to consequently release cytokines within a brief time, thus being suspected to induce abnormal reactions of the living body.

By using a specific antibody against an enterotoxin, an MHC class II protein or the like, the enterotoxin can be removed from a body fluid such as blood, plasma or serum, a culture supernatant, a foodstuff or a beverage but such antibodies are not only expensive but have the drawback that sterilization causes denaturation and serious decreases in adsorptive capacity.

Therefore, the advent has been awaited of an enterotoxin adsorbent which may be produced easily at low cost and will be highly effective.

Incidentally, Japanese Kokai Publication Hei-10-290833 discloses an adsorbent for TSST-1 (toxic shock syndrome toxin-1) comprising a compound having a log P (P denotes a partition coefficient in an octanol-water system) value of not less than 2.50 as immobilized but the literature is reticent about adsorption of an enterotoxin.

SUMMARY OF THE INVENTION

The object of the present invention is to provide an adsorbent with which enterotoxins in body fluids can be efficiently adsorbed and removed, a method for adsorptive removal of an enterotoxin from a body fluid which comprises using said adsorbent, and an enterotoxin adsorption apparatus.

The inventors of the present invention explored in earnest for an adsorbent which may be capable of removing enterotoxins from body fluids with good efficiency. As a result, they discovered that the enterotoxin occurring in a body fluid can be efficiently adsorbed and removed with an adsorbent comprising a compound having a log P value of not less than 2.50 as immobilized on a water-insoluble carrier. The present invention has been developed on the basis of the above finding.

The present invention, therefore, is directed to an enterotoxin adsorbent comprising a compound with a log P, in which P represents a partition coefficient in an octanol-water system, value of not less than 2.50 as immobilized on a water-insoluble carrier.

The present invention is further directed to a method for adsorptive removal of an enterotoxin in a body fluid which comprises contacting an enterotoxin-containing body fluid with an enterotoxin adsorbent, said adsorbent comprising a compound with a log P, in which P represents a partition coefficient in an octanol-water system, value of not less than 2.50 as immobilized on a water-insoluble carrier.

The present invention is further directed to an enterotoxin adsorption apparatus wherein a housing has an inlet and an outlet for a body fluid as well as a means for precluding flowing out of an adsorbent therefrom, and is packed therein an enterotoxin adsorbent, said adsorbent comprising a compound with a log P, in which P represents a partition coefficient in an octanol-water system, value of not less than 2.50 as immobilized on a water-insoluble carrier.

Figure 1:
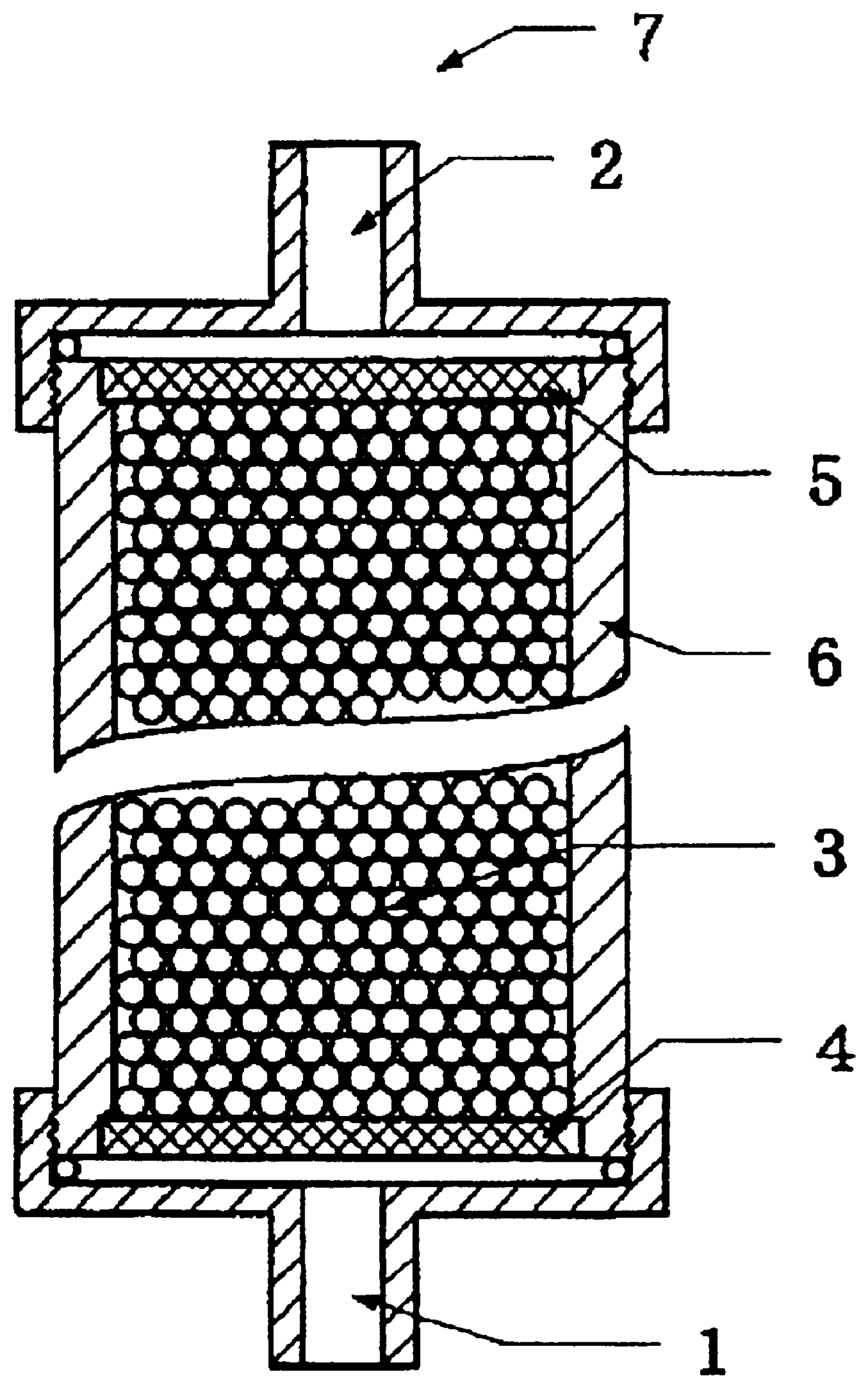
FIG. 1 is a schematic cross-section view showing an enterotoxin adsorption apparatus embodying the principles of the invention.

EXPLANATION OF NUMERIC SYMBOLS 1. body fluid inlet
2. body fluid outlet
3. enterotoxin adsorbent
4. and 5. filter which allows passage of a body fluid but does not allow passage of said enterotoxin adsorbent
6. column
7. enterotoxin adsorption apparatus

DETAILED DESCRIPTION OF THE INVENTION

The enterotoxin in the context of the present invention is a toxin comprising a soluble protein having a molecular weight of 25,000 to 30,000 as produced by *S. aureus*.

The body fluid includes blood, plasma, serum, ascites, lympha, synovial fluid, fractions or components of any of them, and other humoral biological materials.

The log P value is a parameter of hydrophobicity of a compound and the partition coefficient P in the representative octanol-water system is determined in the following manner. Thus, the compound of interest is first dissolved in octanol (or water), an equal quantity of water (or octanol) is then added, and the mixture is shaken with Griffin flask shaker (manufactured by Griffin & George, Ltd.) for 30 minutes. The mixture is then centrifuged at 2000 rpm for 1 to 2 hours and the concentrations of the compound in the octanol layer and the water layer are measured spectrometrically or by GLC at room temperature and atmospheric pressure, among other techniques. Then, the P value is calculated by means of the following equation.

$$P=Coct/Cw$$

Coct: concentration of the compound in octanol layer

Cw: concentration of the compound in water layer

The adsorbent of the invention comprises a water-insoluble carrier and, as supported thereon, a compound having a log P value of not less than 2.50 as determined by the above method.

The log P values of various compounds have so far been measured by many workers and such measured log P values have been compiled by C. Hansch et al. [Partition Coefficients and Their Uses; Chemical Reviews 71, 525 (1971)].

Referring to compounds with unknown measured log P values, the values (Σf) calculated using the hydrophobic fragmental constant f shown in The Hydrophobic Fragmental Constant, Elsevier Sci. Pub. Com., Amsterdam (1977) can be used as a reference. The hydrophobic fragmental constant is a value representing the hydrophobicity of various fragments as determined statistically based on a large number of measured log P values. The sum of f values of various fragments constituting a compound is approximately equal to the log P value. The term log P as used in this invention for any compound with an unknown log P value means the Σf value of the compound.

In the screening for compounds effective for adsorption of enterotoxins, compounds having various log P values were respectively immobilized on a water-insoluble carrier and evaluated for their adsorptive affinity for enterotoxins. As a result, it was found that compounds having log P values not smaller than 2.50, preferably not smaller than 2.80, more preferably not smaller than 3.00, are effective in the adsorption of enterotoxins, while compounds with log P values smaller than 2.50 do not appreciably adsorb enterotoxins. By way of illustration, assuming that an alkylamine is immobilized as said compound on a water-insoluble carrier, the change from n-hexylamine (log P=2.06) to n-octylamine (log P=2.90) leads to a phenomenal increase in the adsorptive affinity for enterotoxins. These findings suggest that the adsorption of an enterotoxin by the adsorbent of the invention is attributable to the hydrophobic interaction between the enterotoxin and the atomic group introduced onto the carrier by immobilization of a compound having a log P value of not less than 2.50 and that any compound having a log P value of less than 2.50 is too low in hydrophobicity to exhibit a sufficiently high adsorptive affinity for enterotoxins.

The compound that can be immobilized on a water-insoluble carrier with advantage in the practice of the invention is not particularly restricted only provided that its log P value is not smaller than 2.50. However, when a compound is immobilized on a carrier by a chemical coupling reaction, a portion of the compound is eliminated in many instances and in case the eliminated group contributes a great deal to the overall hydrophobicity of the compound, that is to say the hydrophobicity of the atomic group immobilized on the carrier is reduced to a Σf value of less than 2.50 due to the eliminated group, the particular compound is not suitable in light of the object and spirit of the invention. A case in point is the immobilization of isopentyl benzoate (Σf=4.15) on a hydroxyl group-containing carrier by a transesterification reaction. In this case, the atomic group actually immobilized on the carrier is $C_6H_5CO$— and this atomic group has a Σf value of less than 1. Whether a compound of this type is suitable as the compound for use in the invention can be simply found by checking to see whether the compound obtainable by substituting hydrogen for the eliminated group has a log P value of not less than 2.50.

The preferred, among compounds having log P values not smaller than 2.50, are unsaturated hydrocarbons, alcohols, amines, thiols, carboxylic acids and derivatives thereof, halides, aldehydes, hydrazides, isocyanates, oxirane ring-containing compounds such as glycidyl ethers, halogenated silanes, and other compounds having functional groups useful for bonding to the carrier. As representative examples of such compounds, there can be mentioned amines such as n-heptylamine, n-octylamine, decylamine, dodecylamine, hexadecylamine, octadecylamine, 2-aminooctene, naphthylamine, phenyl-n-propylamine, diphenylmethylamine, etc.; alcohols such as n-heptyl alcohol, n-octyl alcohol, dodecyl alcohol, hexadecyl alcohol, 1-octen-3-ol, naphthol, diphenylmethanol, 4-phenyl-2-butanol, etc. and glycidyl ethers of such alcohols; carboxylic acids such as n-octanoic acid, nonanoic acid, 2-nonenoic acid, decanoic acid, dodecanoic acid, stearic acid, arachidonic acid, oleic acid, diphenylacetic acid, phenylpropionic acid, etc. and the corresponding acid halides and derivatives such as esters and amides; halides such as octyl chloride, octyl bromide, decyl chloride, dodecyl chloride, etc.; thiols such as octanethiol, dodecanethiol, etc.; halosilanes such as n-octyltrichlorosilane, octadecyltrichlorosilane, etc., and aldehydes such as n-octyl aldehyde, n-capryl aldehyde, dodecyl aldehyde, and so forth.

Aside from the foregoing compounds, compounds such that the hydrogen atom in the hydrocarbon moiety of any of the compounds mentioned by way of example above have been substituted by a halogen atom, a substituent group containing a hetero atom such as N, O or S, a different alkyl group or the like and having log P values not smaller than 2.50, as well as compounds having log P values not less than 2.50 among the compounds listed in the above general review of C. Hansch et al. [Partition Coefficients and Their Uses: Chemical Reviews 71, 525 (1971), pages 555~613] can also be mentioned. For use in the invention, these compounds are not exclusive choices.

These compounds may be used each independently or in a combination of two or more species, optionally even in combination with a compound having a log P value smaller than 2.50.

The water-insoluble carrier as a constituent of the adsorbent of the invention is a material which is solid at atmospheric temperature and pressure and only sparingly soluble in water.

The shape of the water-soluble carrier in the present invention may for example be granular, sheet-like, filamentous or hollow fiber-like, although these are not exclusive choices. The size of the carrier is not particularly restricted, either.

The water-insoluble carrier as a constituent of the adsorbent of the invention includes inorganic matrices such as glass beads, silica gel, etc.; organic matrices such as synthetic polymers, e.g. crosslinked polyvinyl alcohol, crosslinked polyacrylates, crosslinked polyacrylamide, crosslinked polystyrene, etc. and polysaccharides, e.g. crystalline cellulose, crosslinked cellulose, crosslinked agarose, crosslinked dextrin, etc.; and composite matrices comprising organic-organic, organic-inorganic, or other combinations of the above-mentioned matrices, to mention typical examples.

Among these, hydrophilic matrices are preferred because of their comparatively low nonspecific adsorption and good adsorption selectivity for enterotoxins. The term "hydrophilic carrier" is used herein to mean a carrier such that when the compound constituting the carrier is made into a flat plate, the angle of contact between it and water is not greater than 60 degrees. Various techniques are known for measurement of the contact angle of water but as described by Ikeda in his book Jikken Kagaku Sensho (Selected readings in Experimental Chemistry), Chemistry of Colloids, Chapter 4, Thermodynamics of Interfaces, pp. 75 to 104, Mokabo (1986), the most common method comprises placing a drop of water on a flat plate made of the compound and measuring the angle of contact with water. The compound giving such an angle of contact not greater than 60 degrees as measured by the above method includes cellulose, polyvinyl alcohol, saponified ethylene-vinyl acetate copolymer, polyacrylamide, polyacrylic acid, polymethacrylic acid, poly(methyl methacrylate), polyacrylic acid-grafted polyethylene, polyacrylamide-grafted polyethylene, glass and so forth.

These water-insoluble carrier materials preferably have amultiplicity of pores of suitable size, that is to say aporous structure. The carrier having a porous structure includes not only a carrier having spaces (macropores) defined by clusters of microspheres when a basal carrier polymer forms single spherical particles by cohesion of microspheres but also a carrier having micropores formed among the clusters of cores within each microsphere constituting a basal polymer carrier and a carrier having micropores formed when a copolymer having a three-dimensional structure (a polymer network) is swollen in the presence of an organic solvent having an affinity for the polymer.

Furthermore, in consideration of the adsorptive capacity per unit volume of the adsorbent, said water-insoluble carrier having a porous structure is more preferably of the total porosity type than of the surface porosity type and the void volume and specific surface area are preferably as large as possible within limits not detracting from adsorption efficiency.

As a carrier satisfying these preferred requirements, a porous cellulose carrier can be mentioned. The porous cellulose carrier has several meritorious characteristics. Thus, (1) because it has comparatively high mechanical strength and toughness, this carrier does not collapse or give dust in stirring and other operations and even when a body fluid is passed through a column packed with the carrier at a high speed, the carrier is not compacted, thus permitting a high flow rate. Furthermore, the porous structure of the carrier is not easily affected by high-pressure steam sterilization. (2) Because this carrier is made up of cellulose, it is hydrophilic, has a large number of hydroxyl groups available for binding a ligand, and features little nonspecific adsorption. (3) Even if the void volume is increased, an adsorptive capacity as large as that of a soft carrier may be insured because of its comparatively high strength. (4) The carrier ranks high in safety as compared with synthetic polymer and other matrices. Therefore, this carrier is one of the most favorable matrices for use in the present invention, although this is not an exclusive choice. Moreover, the above-mentioned matrices may be used each independently or in the form of a mixture of two or more species.

More preferably, said water-insoluble carrier having a porous structure is characterized in that while the adsorption load may enter its pores with a fairly high probability, the entry of other proteins is precluded as much as possible. Thus, the enterotoxin to be adsorbed by the adsorbent of the invention is a protein having a molecular weight within the range of 25,000 to 30,000 and for efficient adsorption of this protein, the carrier is preferably such that the enterotoxin may find its way into its porous structure in a large ratio but other proteins are prevented from entering the pores. As a molecular weight marker of a substance capable of entering a porous structure, the molecular weight of exclusion limit is generally used. As described in several books (e.g. Hatano Hiroyuki & Hanai Toshihiko: Experimental high Performance Liquid Chromatography, Kagaku Dojin), the molecular weight of exclusion limit means the molecular weight of the smallest of the molecules prevented from entering the pores (entry rejected) in gel permeation chromatography. Molecular weights of exclusion limit have been well documented generally for globular proteins, dextran, polyethylene glycol, etc. and in the case of the carrier for use in the invention, it is appropriate to use the value found for globular proteins.

Investigations undertaken by the inventors using matrices varying in molecular weight of exclusion limit revealed that the range of molecular weights of exclusion limit for globular proteins which is suitable for adsorption of enterotoxins is 5,000 to 600,000. Thus, when a carrier having a molecular weight of exclusion limit of less than 5000 for globular protein is employed, the amount of adsorption of enterotoxins is too small to endorse its practical utility. On the other hand, when the molecular weight of exclusion limit of 600,000 is exceeded, the adsorption of proteins (mostly albumin) other than enterotoxins is increased so that the practical utility of the carrier is low in terms of selectivity. Therefore, the preferred range of molecular weights of exclusion limit for globular protein as the carrier in the present invention is 5,000 to 600,000, with the range of 6,000 to 400,000 being the more preferred and the range of 10,000 to 300,000 being particularly preferred.

Furthermore, the carrier preferably has a functional group which can be used for the ligand-binding reaction. The functional group mentioned above includes but is not limited to hydroxyl, amino, aldehyde, carboxyl, thiol, silanol, amido, epoxy, halogen, succinylimino, and acid anhydride.

The carrier which can be used in the present invention includes both a rigid carrier and a soft carrier. However, when it is used as a constituent of the adsorbent for extracorporeal circulation, it is important that when the adsorbent is packed into a column and the body fluid is passed through it, no plugging should take place. To ensure this, a sufficient mechanical strength is required of the carrier. Therefore, the carrier for use in the invention is more preferably a rigid carrier. The rigid carrier mentioned above means a carrier such that, taking a granular carrier as an example, when a cylindrical column is evenly packed with the carrier and an aqueous fluid is passed, the relation between pressure loss $\Delta P$ and flow rate is linear up to 0.3 kg/cm$^2$ as described hereinafter in Reference Example.

While the adsorbent of the invention can be obtained by immobilizing a compound having a log P value of not less than 2.50 on a water-insoluble porous carrier, various known techniques can be liberally used for the immobilization. However, when the adsorbent of the invention is used for extracorporeal circulation therapy, it is important from safety points of view to minimize the risk of elimination and elution of the ligand during sterilization and therapy and, in this sense, immobilization by covalent bonding is preferred.

Various techniques are available for the adsorptive removal of an enterotoxin from body fluids by means of the adsorbent of the invention. The simplest method comprises withdrawing a body fluid into a bag or the like, mixing the adsorbent with the body fluid to adsorptively remove enterotoxins, and filtering off the adsorbent to recover the fluid having eliminated the enterotoxins. Another method comprises packing the adsorbent into a housing equipped with an inlet and an outlet for a body fluid and, disposed at the outlet, further with a filter which allows passage of a body fluid but intercepts the adsorbent and passing the body fluid through the housing. Whichever desired of the methods can be utilized but the latter method is not only expedient but, when the system is built into an extracorporeal circuit, enables one to remove enterotoxins from a patient's body fluid, particularly the blood, on line and with good efficiency. The adsorbent of the invention is suitable for this method.

In the extracorporeal circuit mentioned above, the adsorbent of the invention may be used independently but may be used in combination with a different extracorporeal therapeutic system. As an example of such combination, an artificial dialysis circuit can be mentioned. Thus, the adsorbent can be used in conjunction with a dialysis treatment.

The enterotoxin adsorption apparatus of the invention, which makes use of the above-described adsorbent of the invention, is now described with reference to FIG. 1 which is a schematic cross-section view showing an embodiment. In FIG. 1, the reference numeral 1 represents a body fluid inlet, 2 a body fluid outlet, 3 an enterotoxin adsorbent according to the invention, 4 and 5 each a filter which allows passage of the body fluid and its components but does not allow passage of said enterotoxin adsorbent, 6 a column, and 7 an enterotoxin adsorption apparatus. It should, however, be understood that the enterotoxin adsorption apparatus is not restricted to such a specific embodiment but may be any apparatus comprising a housing equipped with an inlet and an outlet for a fluid and a means for precluding flowing out of an enterotoxin adsorbent therefrom and, as packed therein, said enterotoxin adsorbent.

The means for precluding flowing out of the adsorbent includes a wire-mesh filter, a nonwoven cloth filter, a cotton pad filter, and so forth. The housing is not particularly restricted in geometry, material or size but one having a columnar configuration is preferred. The preferred housing material withstands a sterilization procedure, thus including silicon-coated glass, polypropylene, poly(vinyl chloride), polycarbonate, polysulfone, polymethylpentene, and so forth. The capacity and size of the housing are preferably 50 to 1500 ml and 2 to 20 cm in diameter, more preferably 100 to 800 ml and 3 to 15 cm in diameter, still more preferably 150 to 400 ml and 4 to 10 cm in diameter.

By means of the adsorbent comprising a compound having a log P value of not less than 2.50 as immobilized on a water-insoluble carrier according to the invention, enterotoxins can be adsorbed and removed from body fluids with good efficiency.

EXAMPLES

The following examples are intended to describe the present invention in further detail and should by no means be construed as defining the scope of the invention.

[Reference Example]

A glass-made cylindrical column (9 mm in. dia.×150 mm long) fitted with a 15 μm (pore size) filter at both ends was uniformly filled with agarose material (product of Bio-Rad; Biogel A-5m, particle diameter 50 to 100 mesh), vinyl polymer material (product of Tosoh Corporation; Toyopearl HW-65, particle diameter 50 to 100 μm) and cellulose material (product of Chisso Corporation; Cellulofine GC-700m, particle diameter 45 to 105 μm). Using a peristaltic pump, water was caused to flow through the column and the relation between flow rate and pressure loss $\Delta P$ was determined. The result is shown in FIG. 2.

Figure 2:
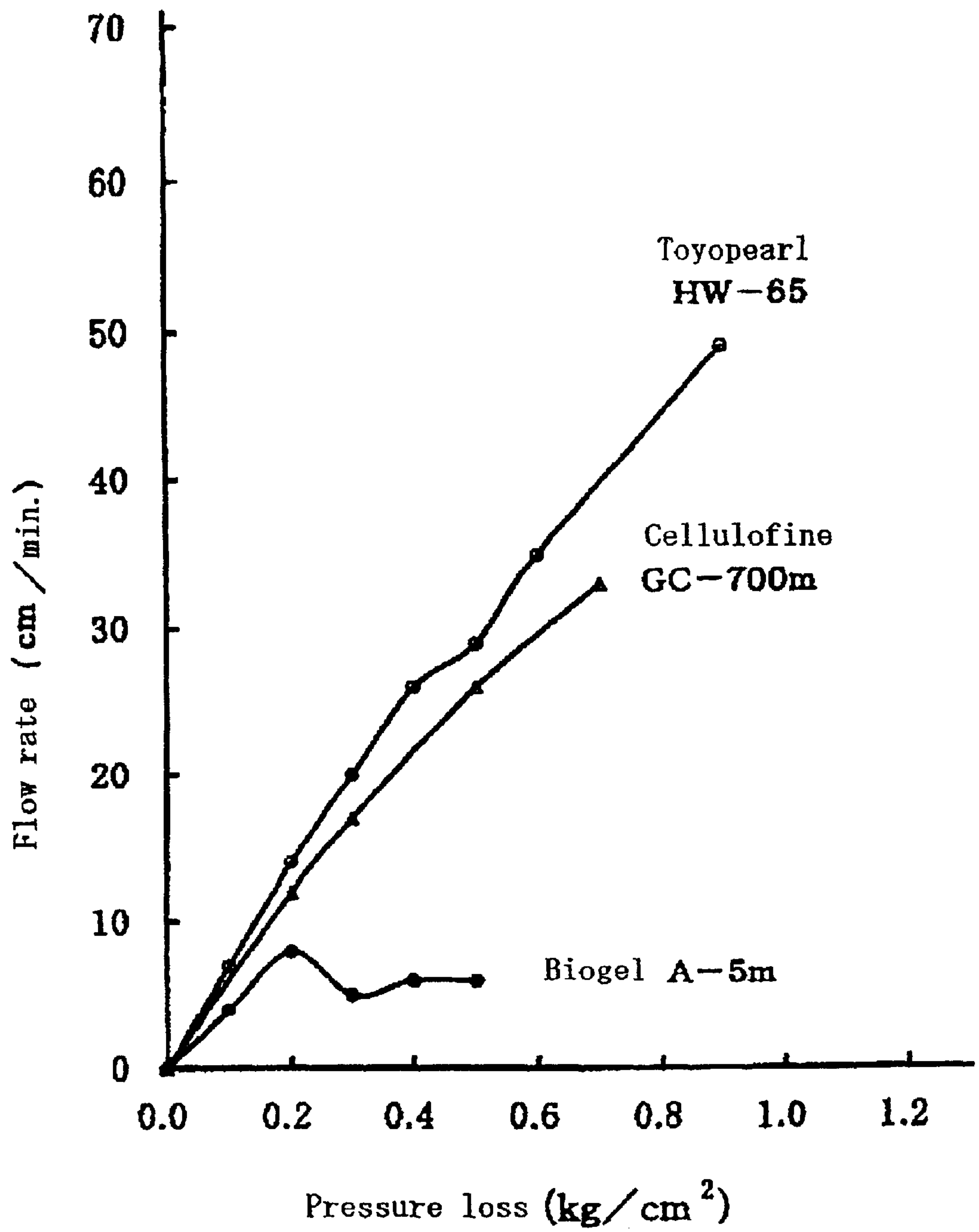
FIG. 2 is a diagrammatic representation of the relation between flow rate and pressure loss as determined for 3 kinds of carrier materials.

It is apparent from FIG. 2 that whereas the flow rate increased in substantial proportion withan increasing pressure in the cases of Toyopearl HW-65 and Cellulofine GC-700m, the flow rate failed to increase owing to compaction even when the pressure was increased in the case of Biogel A-5m. For the purposes of the present invention, any carrier, such as the former two materials, which gives a linear relation between pressure loss $\Delta P$ and flow rate up to 0.3 kg/cm$^2$ is defined as a rigid carrier.

Example 1

To 170 ml of the cellulosic porous carrier Cellulofine GC-200m (product of Chisso Corporation; molecular weight of exclusion limit for globular protein: 140,000) was added sufficient water to make 340 ml. Then, 90 ml of 2 M sodium hydroxide/$H_2O$ was added and the temperature was adjusted to 40° C. To this was added 31 ml of epichlorohydrin, and the reaction was carried out at 40° C. with stirring for 2 hours. After completion of the reaction, the reaction product was rinsed well with water to give epoxidized Cellulofine GC-200m.

To 10 ml of this epoxidized Cellulofine GC-200m was added 200 mg of n-hexadecylamine ($\Sigma f$=7.22), and the reaction was conducted in ethanol under stationary conditions at 45° C. for 6 days. After completion of the reaction, the reaction product was washed thoroughly with ethanol and water in the order mentioned to give n-hexadecylamine-immobilized Cellulofine GC-200m.

To 0.5 ml of the above n-hexadecylamine-immobilized Cellulofine GC-200m was added 3 ml of fetal bovine serum (FBS) containing about 600 pg/ml each of 3 different enterotoxins, namely SEA, SEB, and SEC1, and the mixture was shaken at 37° C. for 2 hours. After 2 hours, the adsorbent was separated from the supernatant and the concentrations of the respective enterotoxins in the supernatant were determined by ELISA.

The ELISA of each enterotoxin was carried out as follows. The primary antibody rabbit anti-SEA (or SEB or SEC) IgG (product of Toxin Technology) was diluted with a coating buffer and distributed onto amicrotiter plate, 100 μl per well. After overnight standing at 4° C., the microtiter plate was washed and 3% bovine serum albumin solution was added, 200 μl per well. The plate was allowed to sit again at room temperature for 2 hours and, then, washed. Thereafter, the standard solutions of the respective enterotoxins and the supernatants before and after incubation were placed in a 100 μl microtiter plate. After 2 hours of sitting at room temperature, the plate was washed. The secondary antibody rabbit anti-SEA (or SEB or SEC) HRP (product of Toxin Technology) was diluted with 1% bovine serum albumin solution and added, 100 μl/well. After 2 hours of sitting at room temperature, the plate was washed. Then, 100 μl/well of o-phenylenediamine solution was added and the plate was allowed to sit at room temperature for 10 minutes.

Thereafter, 100 μl/well of 4 N-sulfuric acid was added and the absorbance at 492 nm was measured. By comparison with the absorbance of the standard solution, the concentration of each enterotoxin was estimated.

Example 2

To 10 ml of the epoxidized Cellulofine GC200m obtained in Example 1 was added 200 mg of n-octylamine (log P=2.90), and the reaction was conducted in 50 (v/v) % ethanol/water at 45° C. under stationary conditions for 6 days. After completion of the reaction, the reaction product was washed thoroughly with 50 (v/v) % ethanol/water, ethanol, 50% (v/v) % ethanol/water, and water in the order mentioned to give n-octylamine-immobilized Cellulofine GC200m.

The above n-octylamine-immobilized Cellulofine GC200m was shaken with FBS containing 3 kinds of enterotoxins just as in Example 1. The adsorbent was separated from the supernatant and the concentration of each enterotoxin in the supernatant was determined by ELISA.

Comparative Example 1

Using n-hexylamine (log P=2.06) in lieu of n-octylamine, the procedure of Example 2 was otherwise faithfully repeated to give n-hexylamine-immobilized Cellulofine GC200m. This n-hexylamine-immobilized Cellulofine GC200m was shaken with FBS containing 3 kinds of enterotoxins just as in Example 1. The adsorbent was separated from the supernatant and the concentration of each enterotoxin in the supernatant was determined by ELISA.

Comparative Example 2

Using n-butylamine (log P=0.97) in lieu of n-octylamine, the procedure of Example 2 was otherwise faithfully repeated to give n-butylamine-immobilized Cellulofine GC200m. This n-butylamine-immobilized Cellulofine GC200m was shaken with FBS containing 3 kinds of enterotoxins just as in Example 1. The adsorbent was separated from the supernatant and the concentration of each enterotoxin in the supernatant was determined by ELISA.

Comparative Example 3

Cellulofine GC-200m was shaken with FBS containing 3 kinds of enterotoxins as in Example 1. The adsorbent was separated from the supernatant and the concentration of each enterotoxin in the supernatant was determined by ELISA.

TABLE 1

| | Concentration of enterotoxin (pg/ml) | | |
|---|---|---|---|
| | SEA | SEB | SEC1 |
| Example 1 | 150 | 130 | 180 |
| Example 2 | 200 | 150 | 210 |
| Comp. Ex. 1 | 565 | 590 | 500 |
| Comp. Ex. 2 | 570 | 600 | 520 |
| Comp. Ex. 3 | 580 | 610 | 540 |

What is claimed is:

1. A method for adsorptive removal of an enterotoxin in a body fluid which comprises contacting an enterotoxin-containing body fluid with an enterotoxin adsorbent to adsorb and remove the enterotoxin, wherein said enterotoxin is at least one selected from the group consisting of staphylococcal enterotoxins A, B, C1, C2, C3, D, E, G, H, and I, said adsorbent comprising a compound with a log P, in which P represents a partition coefficient in an octanol-water system, value of not less than 3.00 as immobilized on a water-insoluble carrier.

2. The method according to claim 1, wherein said water-insoluble carrier is a water-insoluble porous carrier.

3. The method according to claim 2, wherein said water-insoluble porous carrier has a molecular weight of exclusion limit of 50000 to 600000 for globular protein.

4. The method of claim 1, wherein said compound with a log P value of not less than 3.00 is at least one selected from the group consisting of unsaturated hydrocarbons, alcohols, amines, thiols, carboxylic acids and derivatives thereof, halides, aldehydes, hydrazides, isocyanates, oxirine ring-containing compounds, and halogenated silanes.

5. The method according to claim 1, wherein said compound with a log P value of not less than 3.00 is an amine.

6. The method according to claim 1, wherein said compound with a log P value of not less than 3.00 is hexadecylamine.

* * * * *

UNITED STATES PATENT AND TRADEMARK OFFICE

CERTIFICATE OF CORRECTION

PATENT NO. : 6,969,616 B2
APPLICATION NO. : 09/961414
DATED : November 29, 2005
INVENTOR(S) : Hirai et al.

It is certified that error appears in the above-identified patent and that said Letters Patent is hereby corrected as shown below:

Column 1,
Line 32, change "referredtobriefly" to -- referred to briefly --;
Line 44, change "directly-bound" to -- directly bound --;

Column 5,
Line 33, change "amultiplicity" to -- a multiplicity --;
Line 33, change "aporous" to -- a porous --;

Column 8,
Line 14, change "withan" to -- with an --;
Line 53, change "amicrotiter" to -- a microtiter --;

Column 10,
Line 32, change "50000" to -- 5000 --;
Line 38, change "oxirine" to -- oxirane --.

Signed and Sealed this

Eleventh Day of July, 2006

JON W. DUDAS
*Director of the United States Patent and Trademark Office*